(12) United States Patent
Eidson, III

(10) Patent No.: US 11,344,329 B2
(45) Date of Patent: May 31, 2022

(54) VASCULAR GRAFT SECUREMENT APPARATUSES AND RELATED KITS AND METHODS

(71) Applicant: SCOTT & WHITE HEALTHCARE, Temple, TX (US)

(72) Inventor: Jack Leigh Eidson, III, Little River Academy, TX (US)

(73) Assignee: SCOTT & WHITE HEALTHCARE, Temple, TX (US)

( * ) Notice: Subject to any disclaimer, the term of this patent is extended or adjusted under 35 U.S.C. 154(b) by 101 days.

(21) Appl. No.: 15/739,082

(22) PCT Filed: Jun. 24, 2016

(86) PCT No.: PCT/US2016/039273
§ 371 (c)(1),
(2) Date: Dec. 21, 2017

(87) PCT Pub. No.: WO2016/210277
PCT Pub. Date: Dec. 29, 2016

(65) Prior Publication Data
US 2018/0177526 A1    Jun. 28, 2018

Related U.S. Application Data

(60) Provisional application No. 62/185,225, filed on Jun. 26, 2015.

(51) Int. Cl.
*A61B 17/34* (2006.01)
*A61B 17/11* (2006.01)
(Continued)

(52) U.S. Cl.
CPC .......... *A61B 17/3468* (2013.01); *A61B 17/00* (2013.01); *A61F 2/06* (2013.01);
(Continued)

(58) Field of Classification Search
CPC ...... A61F 2/06; A61F 2/064; A61B 2017/044; A61B 2017/0453; A61B 2017/0464;
(Continued)

(56) References Cited

U.S. PATENT DOCUMENTS

| 5,205,459 A | 4/1993 | Brinkerhoff et al. |
| 5,755,697 A * | 5/1998 | Jones ................. A61B 17/3415 604/174 |

(Continued)

OTHER PUBLICATIONS

International Search Report and Written Opinion issued in International Application No. PCT/US2016/39273, dated Sep. 13, 2016.

*Primary Examiner* — Diane D Yabut
*Assistant Examiner* — Christian D Knauss
(74) *Attorney, Agent, or Firm* — Norton Rose Fulbright US LLP

(57) ABSTRACT

Some of the present apparatuses include a flexible vascular graft defining a lumen and a hub having a distal end configured to penetrate a blood vessel, a proximal end, and a wall extending between the distal end and the proximal end that defines an interior passageway. In some apparatuses, the vascular graft is non-removably coupled to the hub, and the lumen of the vascular graft is in communication with the interior passageway of the hub. Some apparatuses include one or more helical protrusions fixed in relation to the wall and configured to secure the hub relative to the blood vessel, each of the one or more helical protrusions extending away from the interior passageway. In some apparatuses, the wall has an outer surface defining an annular recess that extends around the wall, the recess configured to receive at least a portion of a wall of the blood vessel.

17 Claims, 8 Drawing Sheets

(51) Int. Cl.
  *A61F 2/06* (2013.01)
  *A61B 17/00* (2006.01)
  *A61B 17/064* (2006.01)
  *A61B 17/22* (2006.01)

(52) U.S. Cl.
  CPC ...... *A61F 2/064* (2013.01); *A61B 2017/0648* (2013.01); *A61B 2017/1107* (2013.01); *A61B 2017/1135* (2013.01); *A61B 2017/22038* (2013.01); *A61B 2017/3488* (2013.01)

(58) Field of Classification Search
  CPC ............ A61B 2017/0648; A61B 17/11; A61B 2017/1107; A61B 2017/1135; A61B 17/0401; A61B 17/3468; A61B 2017/3488
  See application file for complete search history.

(56) References Cited

U.S. PATENT DOCUMENTS

| | | | |
|---|---|---|---|
| 5,824,071 A * | 10/1998 | Nelson | A61B 17/320016 606/194 |
| 5,893,369 A * | 4/1999 | LeMole | A61B 17/11 606/184 |
| 6,030,395 A * | 2/2000 | Nash | A61B 17/11 606/153 |
| 6,596,003 B1 | 7/2003 | Realyvasquez, Jr. et al. | |
| 6,645,225 B1 * | 11/2003 | Atkinson | A61B 17/0057 128/898 |
| 7,695,483 B2 | 4/2010 | Nash et al. | |
| 7,749,239 B2 | 7/2010 | De Winter | |
| 8,974,379 B2 * | 3/2015 | Hashiba | A61B 17/3421 600/184 |
| 2001/0004699 A1 * | 6/2001 | Gittings | A61B 17/11 606/153 |
| 2001/0037113 A1 * | 11/2001 | Justin | A61B 17/864 606/916 |
| 2003/0014064 A1 * | 1/2003 | Blatter | A61B 17/0643 606/153 |
| 2003/0078562 A1 | 4/2003 | Makower et al. | |
| 2003/0153933 A1 | 8/2003 | Bolduc et al. | |
| 2004/0093057 A1 | 5/2004 | Bolduc et al. | |
| 2006/0089707 A1 | 4/2006 | Vassiliades et al. | |
| 2006/0259050 A1 * | 11/2006 | De Winter | A61B 17/0057 606/153 |
| 2009/0112062 A1 * | 4/2009 | Bakos | A61B 1/00087 600/114 |
| 2011/0264117 A1 * | 10/2011 | Layton | A61B 17/11 606/139 |
| 2012/0109168 A1 | 5/2012 | Gerhardt | |
| 2013/0060267 A1 * | 3/2013 | Farnan | A61B 17/11 606/153 |
| 2015/0038999 A1 * | 2/2015 | Gartner | A61B 17/00234 606/153 |
| 2017/0202575 A1 * | 7/2017 | Stanfield | A61B 17/3478 |

* cited by examiner

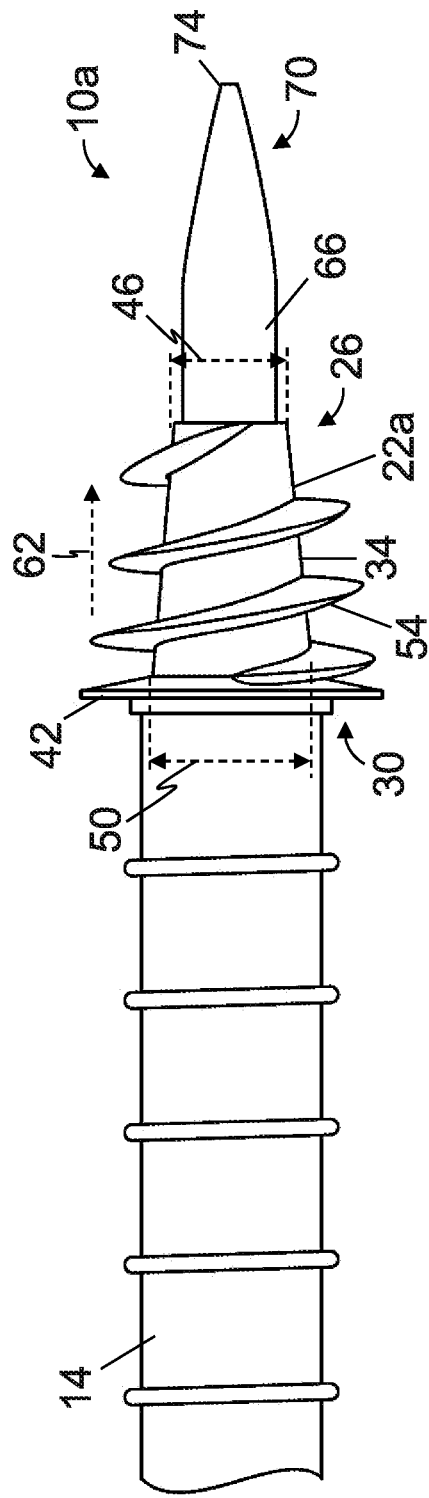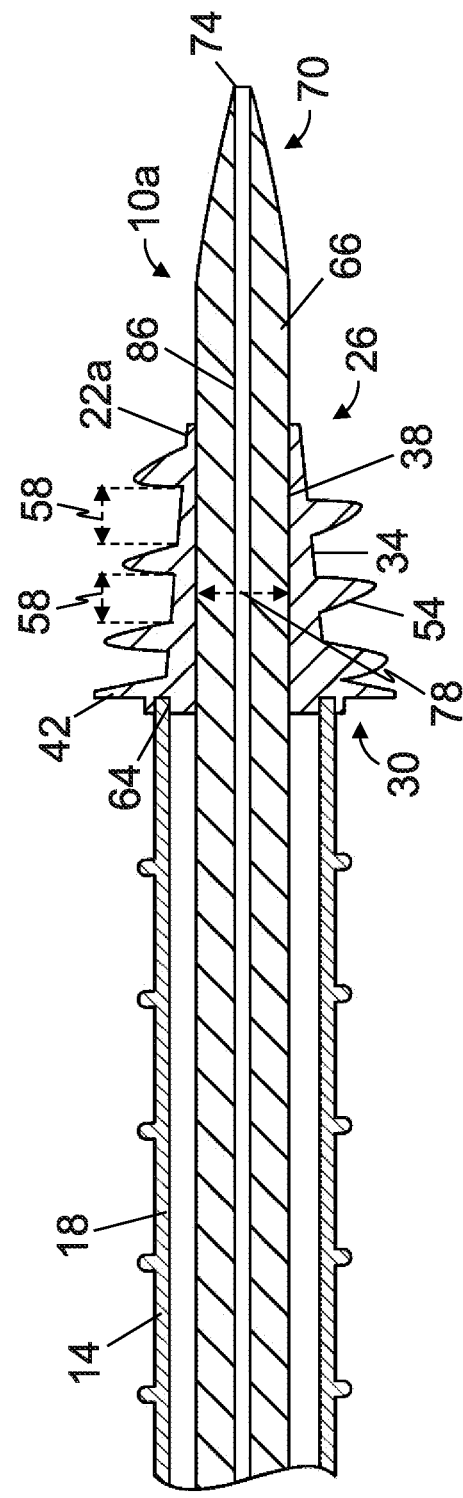
FIG. 1A
FIG. 1B

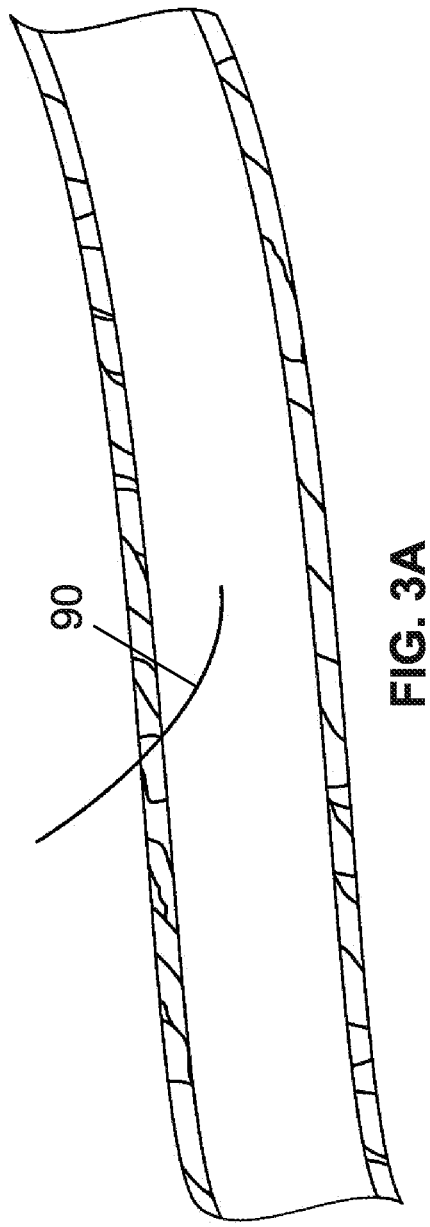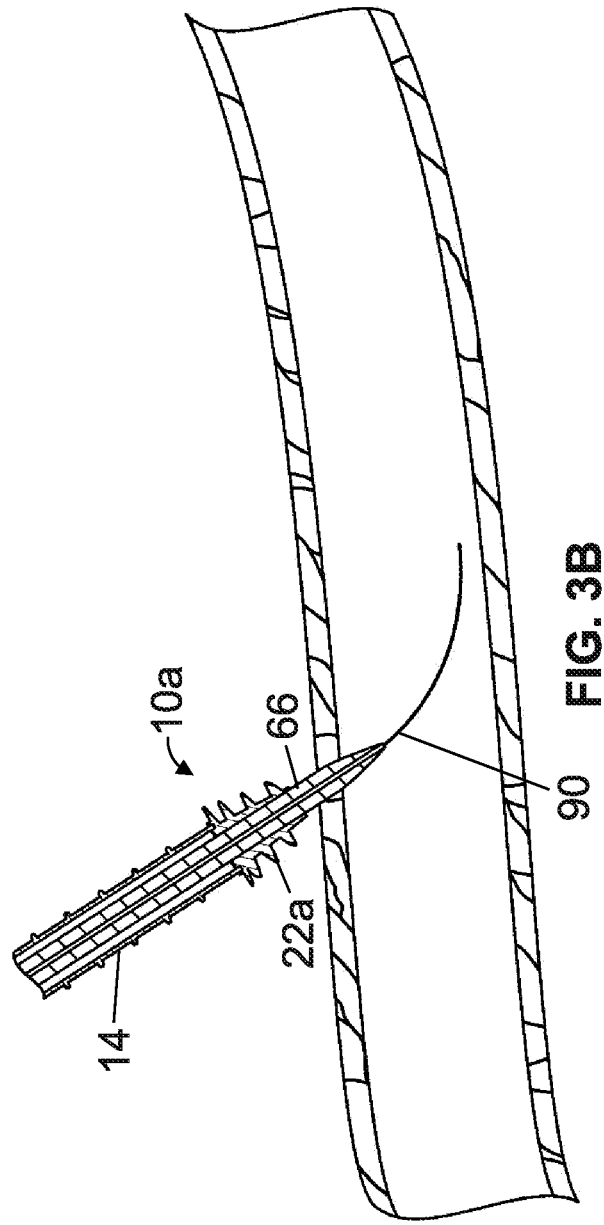

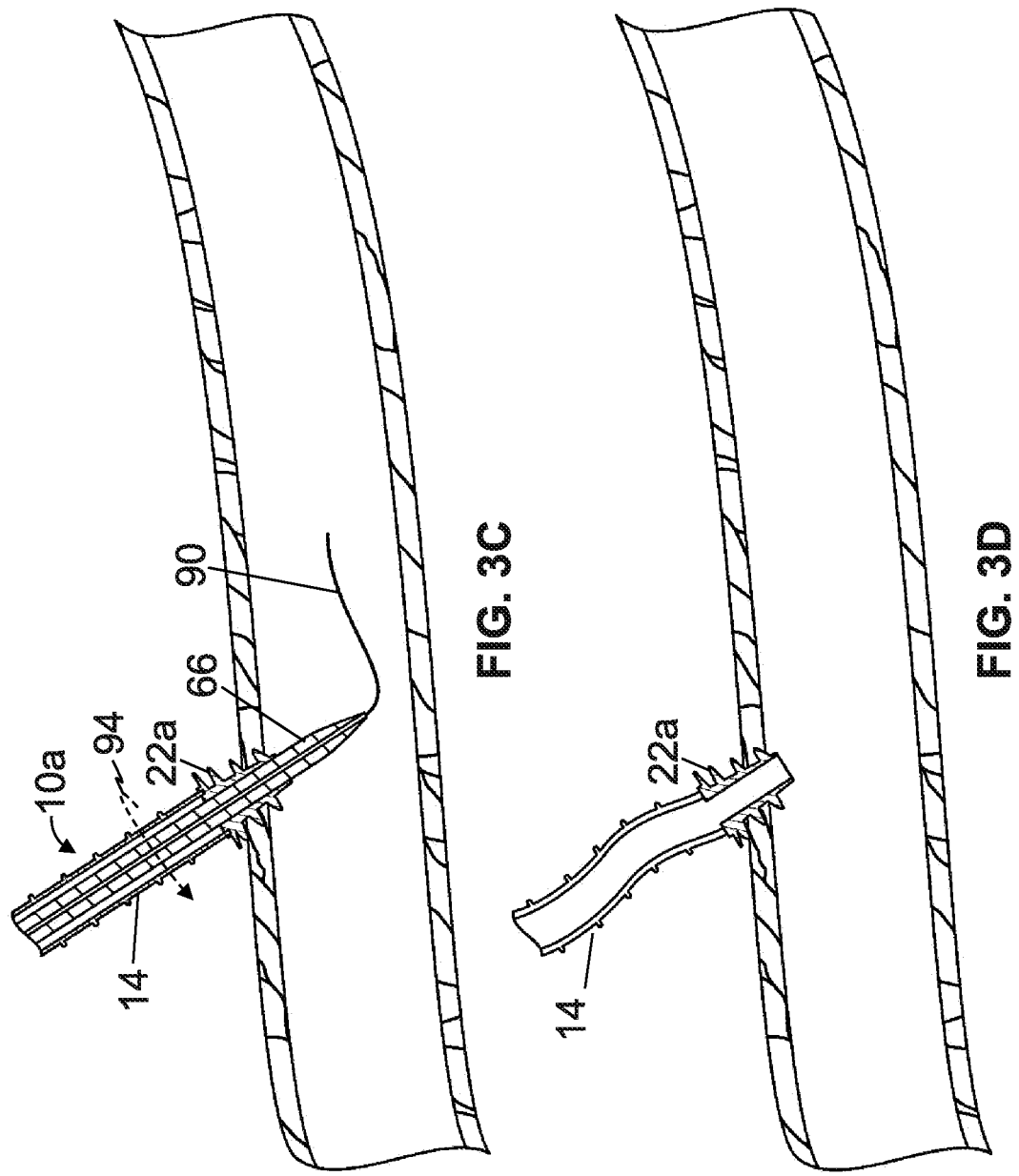

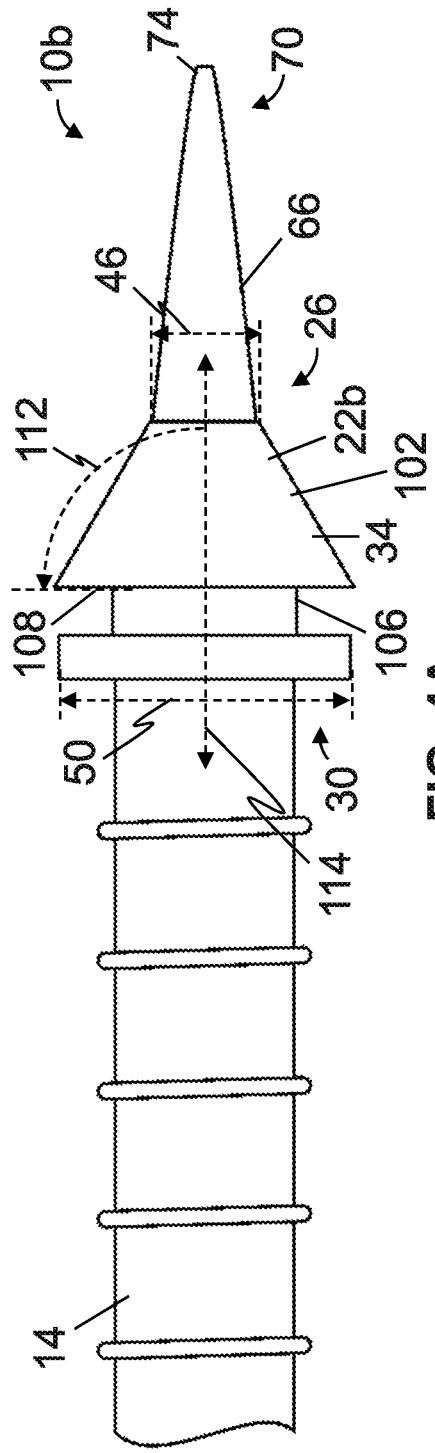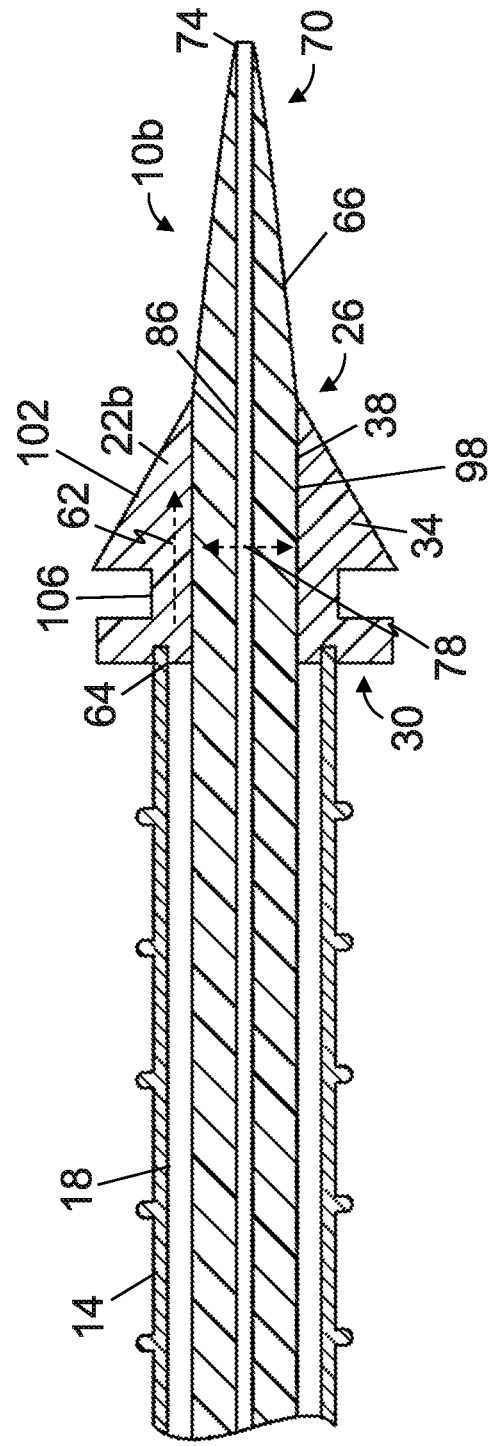
FIG. 4A
FIG. 4B

VASCULAR GRAFT SECUREMENT APPARATUSES AND RELATED KITS AND METHODS

CROSS-REFERENCE TO RELATED APPLICATION

This application is a national stage application under 35 U.S.C. § 371 of International Application No. PCT/US2016/039273, filed Jun. 24, 2016, which claims the benefit of priority to U.S. Provisional Patent Application No. 62/185,225, filed Jun. 26, 2015 and entitled "VASCULAR GRAFT SECUREMENT APPARATUSES AND RELATED KITS AND METHODS," the entire contents of each of which are hereby incorporated by reference in their entireties.

BACKGROUND

1. Field of Invention

The present invention relates generally to vascular bypass surgery, and more specifically, but not by way of limitation, to apparatuses, kits, and methods for securing vascular grafts to blood vessels.

2. Description of Related Art

Despite advances in endovascular surgery, vascular bypass surgeries (e.g., aortofemoral, aortomesenteric, and aortorenal bypass surgeries) are still often performed to treat certain vascular conditions, such as, for example, atherosclerotic occlusive disease. Such bypass surgeries may be prevalent because, in many instances, such bypass surgeries offer relatively high long-term patency rates. Unfortunately, while bypass surgeries may often be life- or limb-saving, such bypass surgeries still possess significant mortality rates—in some instances, having mortality rates of 5% or higher.

Such significant mortality rates may be driven, in part, by issues associated with existing vascular bypass devices and procedures. For example, many existing vascular bypass devices include a conduit that may require an opening, such as an arteriotomy or veinotomy, to be made in a blood vessel wall before the conduit can be operatively connected to the blood vessel. To minimize blood loss through such an opening, the blood vessel must generally be clamped, which is an inherently dangerous procedure (particularly when operating on a large artery, such as the aorta).

Examples of vascular bypass or access devices are disclosed in: (1) U.S. Pat. No. 5,755,697; (2) U.S. Pat. No. 7,749,239; (3) U.S. Pat. No. 7,695,483; (4) Pub. No. US 2006/0089707; and (5) Pub. No. US 2013/0060267.

SUMMARY

Some embodiments of the present apparatuses are configured, through a penetrator disposable within a lumen of a vascular graft and/or within an interior passageway of a hub coupled to the vascular graft, to provide for a vascular bypass via the hub without requiring an existing opening, such as a arteriotomy or veinotomy, in the blood vessel (e.g., other than an opening provided for by a guide wire) and/or without requiring vascular clamping or occlusion of the blood vessel.

Some embodiments of the present apparatuses are configured, through a vascular graft defining a lumen and a hub defining an interior passageway, where the vascular graft is non-removably coupled to the hub such that the lumen of the vascular graft is in communication with the interior passageway of the hub, to facilitate, for example, use of the apparatuses as a permanent implant, a fluid-tight coupling between the vascular graft and the hub, and/or the like.

Some embodiments of the present apparatuses are configured, through a hub having a (e.g., tapered) wall and one or more helical protrusions extending away from the wall, to facilitate, for example, securement of the hub relative to a wall of a blood vessel (e.g., via radial forces between the wall of the blood vessel and the wall of the hub and/or compressive forces between the wall of the blood vessel and adjacent portions of the one or more helical protrusions). Some embodiments of the present apparatuses are configured, through a hub having a (e.g., tapered) wall defining an annular recess extending around the wall, to facilitate, for example, securement of the hub relative to a wall of a blood vessel (e.g., via radial forces between the wall of the blood vessel and the wall of the hub and/or compressive forces between the wall of the blood vessel and portions of the wall of the hub within the recess).

Some embodiments of the present apparatuses may be configured for laparoscopic vascular bypass or anastomosis procedures (e.g., through a laparoscopic port, for example, in an abdominal wall) by obviating the need for vascular clamping and/or occlusion (which may be difficult and/or dangerous through laparoscopic means).

Some embodiments of the present apparatuses for securing a vascular graft to a blood vessel comprise: a flexible vascular graft defining a lumen and a hub having a distal end configured to penetrate a blood vessel, a proximal end, a wall extending between the distal end and the proximal end that defines an interior passageway, and one or more helical protrusions fixed in relation to the wall and configured to secure the hub relative to the blood vessel, each of the one or more helical protrusions extending away from the interior passageway, where the vascular graft is couplable to the hub such that the lumen of the vascular graft is in communication with the interior passageway of the hub.

In some embodiments, for each of the one or more helical protrusions, a longitudinal distance between adjacent portions of the helical protrusions decreases along a direction from the distal end of the hub to the proximal end of the hub.

In some embodiments, the proximal end of the hub defines a flange. In some embodiments, the flange defines one or more openings, each configured to receive a suture.

Some embodiments of the present apparatuses for securing a vascular graft to a blood vessel comprise: a flexible vascular graft defining a lumen and a hub having a distal end configured to penetrate a blood vessel, a proximal end, and a wall extending between the distal end and the proximal end, the wall having an inner surface defining an interior passageway and an outer surface defining an annular recess that extends around the wall, the recess configured to receive at least a portion of a wall of the blood vessel, where the vascular graft is couplable to the hub such that the lumen of the vascular graft is in communication with the interior passageway of the hub.

In some embodiments, the recess is rotationally symmetrical about a longitudinal axis of the hub. In some embodiments, the recess is defined by the wall of the hub closer to the proximal end of the hub than to the distal end of the hub. In some embodiments, the recess is defined in fixed relation to the wall. In some embodiments, a distal-most portion of the wall within the recess is tangent to a line that is angularly disposed at an angle of 90 degrees or larger relative to a longitudinal axis of the hub.

In some embodiments, the vascular graft is non-removably coupled to the hub. In some embodiments, the vascular graft is coupled to the proximal end of the hub. In some embodiments, the vascular graft is coupled to the hub such that at least a portion of the hub is received within the lumen of the vascular graft. Some embodiments comprise a crimped connection between the vascular graft and the hub. Some embodiments comprise a welded connection between the vascular graft and the hub. In some embodiments, the vascular graft comprises at least one of: woven polyester and expanded polytetrafluoroethylene.

In some embodiments, the distal end of the hub has a first transverse dimension, and the proximal end of the hub has a second transverse dimension that is larger than the first transverse dimension. In some embodiments, the interior passageway of the hub tapers in a transverse dimension along a direction from the proximal end of the hub to the distal end of the hub. In some embodiments, the hub is rigid. In some embodiments, the hub is monolithic. In some embodiments, the hub comprises a biochemically non-reactive material.

Some embodiments comprise a penetrator configured to penetrate the blood vessel. In some embodiments, the penetrator defines an interior passageway sized for a guide wire. In some embodiments, the penetrator is disposable through the lumen of the vascular graft and through the interior passageway of the hub. In some embodiments, the penetrator is couplable to the hub such that rotation of the penetrator rotates the hub.

Some embodiments of the present kits comprise: a vascular graft defining a lumen and a hub having a distal end, a proximal end, a wall extending between the distal end and the proximal end that defines an interior passageway, and one or more helical protrusions fixed in relation to the wall, each extending away from the interior passageway, where the vascular graft is non-removably coupled to the hub, and the lumen of the vascular graft is in communication with the interior passageway of the hub.

Some embodiments of the present kits comprise: a vascular graft defining a lumen and a hub having a distal end, a proximal end, and a wall extending between the distal end and the proximal end, the wall having an inner surface defining an interior passageway and an outer surface defining an annular recess that extends around the wall, the recess configured to receive at least a portion of a wall of a blood vessel, where the vascular graft is non-removably coupled to the hub, and the lumen of the vascular graft is in communication with the interior passageway of the hub.

Some embodiments comprise a penetrator defining an interior passageway sized for a guide wire. Some embodiments comprise a guide wire.

Some embodiments of the present methods for securing a vascular graft to a blood vessel comprise: inserting a distal end of a penetrator into a blood vessel, the penetrator disposed within a lumen of a vascular graft and within an interior passageway of a hub coupled to the vascular graft, the hub having a distal end configured to penetrate the blood vessel, a proximal end, a wall extending between the distal end and the proximal end that defines an interior passageway, and one or more helical protrusions fixed in relation to the wall, each extending away from the interior passageway, rotating the hub relative to the blood vessel to secure the hub within the blood vessel, and removing the penetrator from the interior passageway of the hub and through the lumen of the vascular graft.

In some embodiments, rotating the hub relative to the blood vessel comprises rotating the penetrator relative to the blood vessel to rotate the hub relative to the blood vessel. Some embodiments comprise suturing the hub to the blood vessel.

Some embodiments of the present methods for securing a vascular graft to a blood vessel comprise: inserting a distal end of a penetrator into a blood vessel, the penetrator disposed within a lumen of a vascular graft and within an interior passageway of a hub coupled to the vascular graft, the hub having a distal end configured to penetrate the blood vessel, a proximal end, and a wall extending between the distal end and the proximal end, the wall having an inner surface defining an interior passageway and an outer surface defining an annular recess that extends around the wall, urging at least a portion of a wall of the blood vessel into the recess of the hub, and removing the penetrator from the interior passageway of the hub and through the lumen of the vascular graft.

In some embodiments, urging the at least a portion of the wall of the blood vessel into the recess of the hub comprises tensioning one or more sutures disposed into the wall of the blood vessel and around at least a portion of the hub.

Some embodiments comprise clamping the vascular graft.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1A is a side view of a first embodiment of the present apparatuses.

FIGS. 1B and 1C are cross-sectional side and front views, respectively, of the apparatus of FIG. 1A.

FIGS. 3A-3D depict steps of one embodiment of the present methods.

FIG. 4A is a side view of a second embodiment of the present apparatuses.

FIGS. 4B and 4C are cross-sectional side and front views, respectively, of the apparatus of FIG. 4A.

DETAILED DESCRIPTION OF ILLUSTRATIVE EMBODIMENTS

Figure 1C:
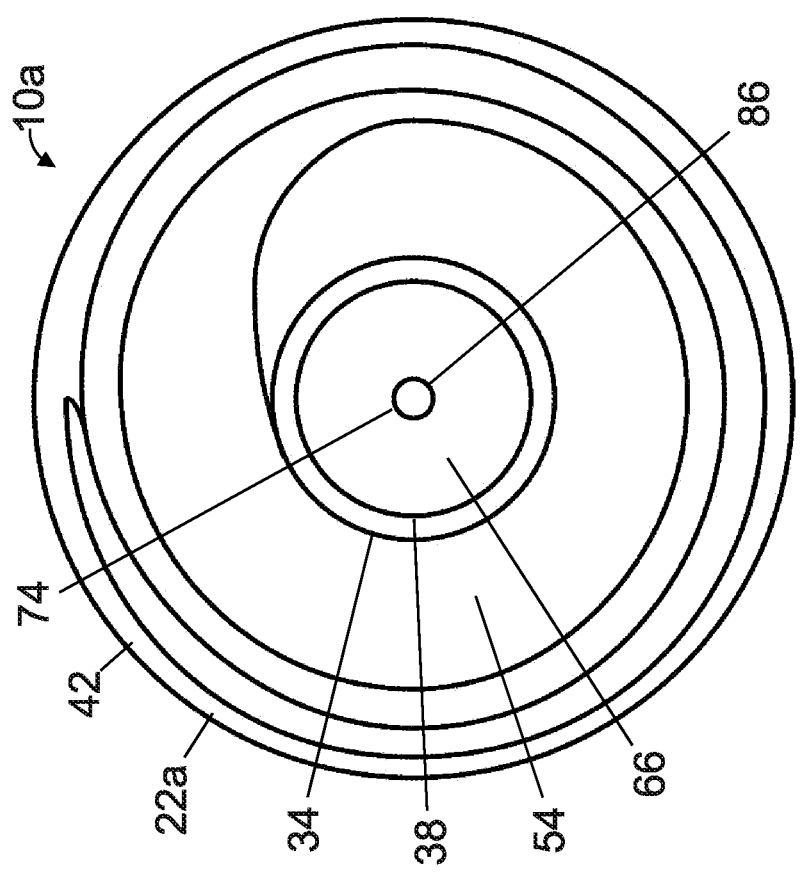

Referring now to the figures, and more particularly to FIGS. 1A-1C, shown and designated by the reference numeral 10a is one embodiment of the present apparatuses. In the depicted embodiment, and as described in detail below, apparatus 10a is configured to secure a vascular graft 14 relative to a blood vessel (e.g., an artery, vein, and/or the like), such as during a vascular bypass or anastomosis procedure. For example, in this embodiment, apparatus 10a comprises a vascular graft 14 defining a lumen 18. The vascular graft may be flexible. Respective vascular grafts (e.g., 14) of the present apparatuses (e.g., 10a) may comprise any suitable vascular graft, such as, for example, a vascular graft having a length from 14 centimeters (cm) to 140 cm (and including every integer and half-integer between 14 and 140 cm), having a lumen (e.g., 18) diameter from 3 millimeters (mm) to 14 mm (and including every integer and tenth of an integer between 3 and 14 mm), and comprising any suitable material, such as, for example, woven polyester, expanded polytetrafluoroethylene, polyethylene terephthalate, and/or the like.

In the depicted embodiment, apparatus 10a comprises a hub 22a having a distal end 26, a proximal end 30, and a wall 34 extending between the distal end and the proximal end that defines an interior passageway 38 through the hub. The hub may be rigid. In the embodiment shown, distal end 26 is configured to penetrate (e.g., be disposed into, but not necessarily through) a wall of a blood vessel, such as via one or more helical protrusions 54 of hub 22a, a taper of the hub from proximal end 30 to the distal end, and/or the like, as described below. In this embodiment, proximal end 30 of hub 22a defines a flange 42 that extends from wall 34 and away from interior passageway 38. In the depicted embodiment, flange 42 may be configured (e.g., sized and located relative to other portions of hub 22a) to physically limit a penetration depth of the hub into a blood vessel. While, in the embodiment shown and as described below, hub 22a is configured to be secured relative to a blood vessel without the use of sutures, in some embodiments of the present apparatuses, a flange (e.g., 42) of a respective hub (e.g., 22a) may define one or more openings, each configured to receive a suture, so as, for example, to provide for enhanced securement of the respective hub to a blood vessel.

In the embodiment shown, distal end 26 of hub 22a has a first transverse dimension 46 and proximal end 30 of the hub has a second transverse dimension 50 (e.g., excluding flange 42 and one or more helical protrusions 54, if present) that is larger than the first transverse dimension. For example, the hub, and more particularly, wall 34 of the hub, tapers from the proximal end to the distal end (e.g., to define a taper angle that is greater than any one of, or between any two of: 1, 2, 3, 4, 5, 6, 7, 8, 9, 10, 15, 20, 25, 30, 35, 40, 45, or more degrees). In at least this way, as hub 22a penetrates a wall of a blood vessel, the hub may dilate an opening in the wall of the blood vessel (e.g., whether the opening is made by distal end 26 of the hub, a guide wire 90, a penetrator 66, and/or the like), so as, for example, to facilitate a seal and/or provide for a radial retention force between the hub and the wall of the blood vessel.

In this embodiment, hub 22a includes one or more helical protrusions 54 (e.g., one helical protrusion, as shown) fixed in relation to wall 34, each of the one or more helical protrusions extending away from interior passageway 38. As used in this disclosure, "helical" is not limited to describing only those structures that satisfy the mathematical definition of a helix. For example, in the depicted embodiment, each of one or more helical protrusions 54 is helical in that at least a portion of the protrusion extends along wall 34 of hub 22a in both a circumferential direction and a longitudinal direction, such that, for example, in some embodiments, the protrusion, or a portion thereof, may surround the hub without closing on itself.

Figure 2:
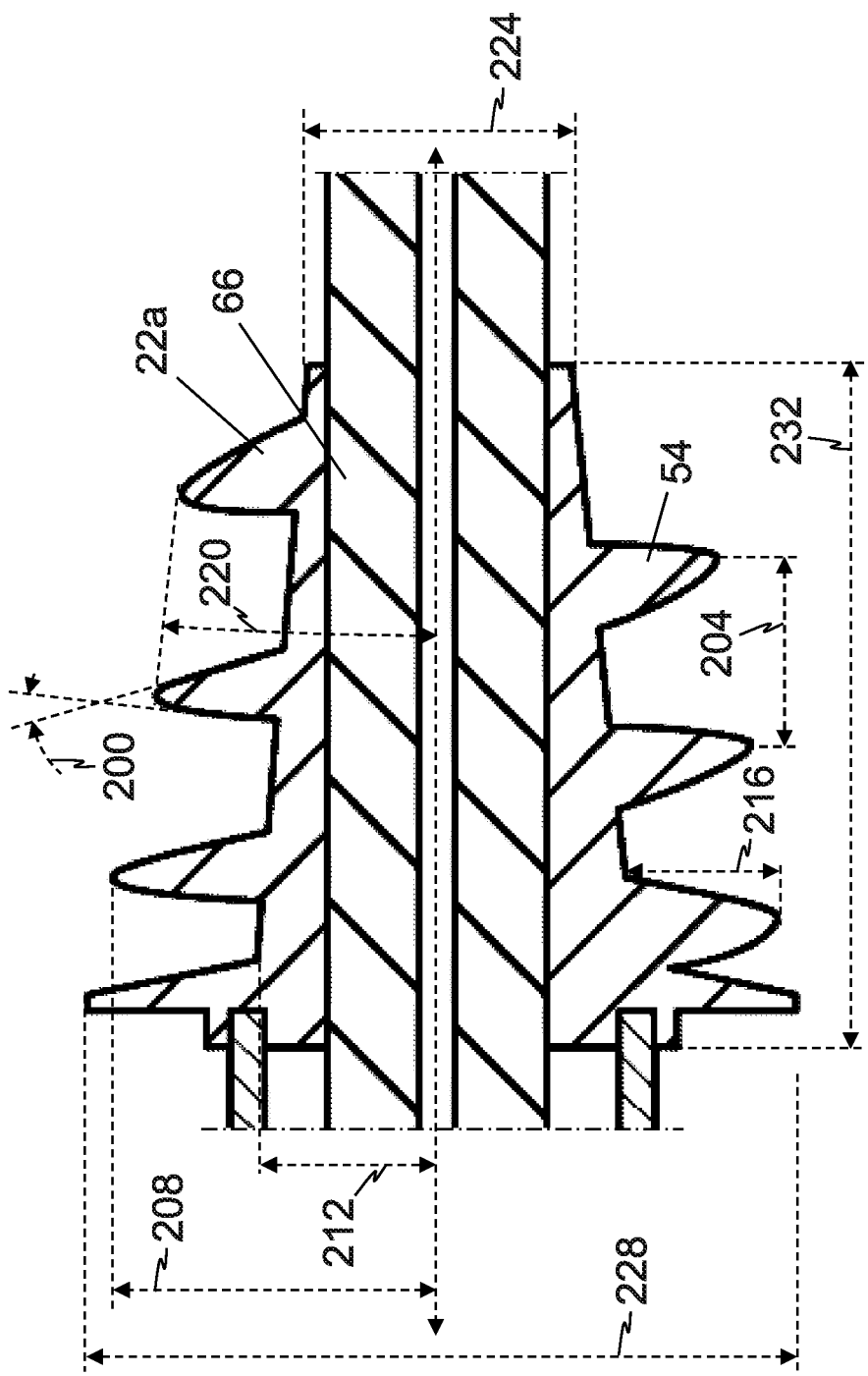
FIG. 2 is a cross-sectional side view of a hub, which may be suitable for use in some embodiments of the present apparatuses.

One or more helical protrusions (e.g., 54) of some embodiments of the present apparatuses (e.g., 10a) may each be similar to and/or characterized as a thread; therefore, such helical protrusion(s) may be described with reference to thread characteristics. To illustrate, and referring additionally to FIG. 2, helical protrusion(s) (e.g., 54) may have any suitable:
1. thread angle(s) (e.g., 200), such as, for example, thread angle(s) that are greater than or equal to any one of, or between any two of: 10, 15, 20, 25, 30, 35, 40, 45, 50, 55, 60, 65, 70, 75, 80, 85, 90, and/or more degrees;
2. lead(s) and/or pitch(es) (e.g., 204), such as, for example, lead(s) and/or pitch(es) that are greater than or equal to any one of, or between any two of: 1, 2, 3, 4, 5, 6, 7, 8, 9, 10, 11, 12, 13, 14, 15, 16, 17, 18, 19, 20 and/or more mm (for a hub having one helical protrusion, a lead may be the same as a pitch);
3. major diameter(s) (e.g., two times distance 208, which is measured from an axis the respective helical protrusion), such as, for example, major diameter(s) that are greater than or equal to any one of, or between any two of: 5, 6, 7, 8, 9, 10, 11, 12, 13, 14, 15, 16, 17, 18, 19, 20, 21, 22, 23, 24, 25, 26, 27, 28, 29, 30, and/or more mm;

4. minor diameter(s) (e.g., two times distance 212, which is measured from an axis of the respective helical protrusion), such as, for example, minor diameter(s) that are greater than or equal to any one of, or between any two of: 5, 6, 7, 8, 9, 10, 11, 12, 13, 14, 15, 16, 17, 18, 19, 20, 21, 22, 23, 24, 25, 26, 27, 28, 29, 30, and/or more mm;
5. thread depth(s) (e.g., 216), such as, for example, thread depth(s) that are greater than or equal to any one of, or between any two of: 1, 2, 3, 4, 5, 6, 7, 8, 9, 10, 11, 12, 13, 14, 15, and/or more mm;
6. taper angle(s) (e.g., 220, which is measured from an axis of the respective helical protrusion), such as, for example, taper angle(s) that are greater than or equal to any one of, or between any two of: 0, 1, 2, 3, 4, 5, 6, 7, 8, 9, 10, 15, 20, 25, 30, 35, 40, 45, and/or more degrees;
7. thread form(s), such as, for example, thread form(s) that are square, rectangular, trapezoidal, triangular, otherwise polygonal, circular, elliptical, and/or otherwise rounded;
8. number of starts, such as, for example, 1, 2, 3, 4, or more starts (e.g., a hub having two helical protrusions may be described as having two starts); and/or
9. handedness;

and such characteristic(s) for a given helical protrusion may vary along a length of a hub (e.g., 22a).

In the embodiment shown, one or more helical protrusions 54 are configured to secure hub 22a relative to a blood vessel. For example, in this embodiment, distal end 26 of hub 22a may be pressed against, disposed within, and/or disposed through a wall of a blood vessel, and the hub may be rotated relative to the wall of the blood vessel, whereby one or more helical protrusions 54 may urge the wall of the blood vessel towards proximal end 30 of the hub, thereby securing the wall of the blood vessel relative to the hub (e.g., between adjacent portions of the one or more helical protrusions, against flange 42, and/or the like), as if by threading the hub into the wall of the blood vessel.

In the depicted embodiment, for each of one or more helical protrusions 54, a longitudinal distance 58 between adjacent portions of the helical protrusion (e.g., similar to a lead), increases along a direction (e.g., generally indicated by arrow 62) from proximal end 30 of hub 22a to distal end 26 of the hub. In this way, for example, a wall of a blood vessel, or a portion thereof, may be received between adjacent portions of one or more helical protrusions 54 (e.g., whether the adjacent portions are portions of a same helical protrusion, as shown, or portions of separate helical protrusions), and hub 22a may be rotated relative to the wall of the blood vessel such that, as the wall of the blood vessel, or portion thereof, is urged towards proximal end 30 of the hub by the adjacent portions, the wall of the blood vessel, or portion thereof, may be compressed between the adjacent portions, which may facilitate a seal and/or provide for a compressive retention force between the hub and the wall of the blood vessel.

In the embodiment shown, hub 22a is monolithic (e.g., distal end 26, proximal end 30, wall 34, flange 42, and one or more helical protrusions 54 are each unitary and/or integrally formed with one another), such that, for example, the hub is robust and/or leak-resistant. In this embodiment, hub 22a comprises (e.g., is formed from and/or includes a coating of) a biochemically non-reactive material. Such biochemically non-reactive materials may comprise any suitable biochemically non-reactive material, whether metallic (e.g., stainless steel, a cobalt alloy, a titanium alloy) and/or non-metallic (silicone, polyethylene, polyvinyl chloride, polyurethane, and/or the like).

Hubs (e.g., 22a, 22b, and/or the like) of the present devices (e.g., 10a, 10b, and/or the like) can comprise any suitable dimensions, such as, for example, a minimum transverse dimension (e.g., 224) that is greater than or equal to any one of, or between any two of: 5, 6, 7, 8, 9, 10, 11, 12, 13, 14, 15, 16, 17, 18, 19, 20, 21, 22, 23, 24, 25, 26, 27, 28, 29, 30, or more mm, a maximum transverse dimension (e.g., 228) that is greater than or equal to any one of, or between any two of: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more mm, a length (e.g., 232) that is greater than any one of, or between any two of: 5, 6, 7, 8, 9, 10, 11, 12, 13, 14, 15, 16, 17, 18, 19, 20, 21, 22, 23, 24, 25, 26, 27, 28, 29, 30, or more mm, and/or the like.

In the depicted embodiment, vascular graft 14 is couplable to hub 22a such that lumen 18 of the vascular graft is in communication with interior passageway 38 of the hub (FIG. 1B). For example, in the embodiment shown, vascular graft 14 is coupled to proximal end 30 of hub 22a such that lumen 18 of the vascular graft is in communication with interior passageway 38 of the hub. In this embodiment, vascular graft 14 is couplable to hub 22a such that at least a portion of the hub is received within lumen 18 of the vascular graft. For example, in the depicted embodiment, proximal end 30 of hub 22a defines a (e.g., annular) recess 64 configured to receive at least a portion of vascular graft 14 (e.g., such that a portion of the hub bounded by the recess is received within lumen 18 of the vascular graft) when the vascular graft is coupled to the hub, which may facilitate a sealed and/or enhanced connection between the vascular graft and the hub. In some embodiments, a connection between a respective vascular graft (e.g., 14) and a respective hub (e.g., 22a) may be sealed, for example, via a polymer sealant disposed at an interface between the respective vascular graft and the respective hub.

In the embodiment shown, vascular graft 14 is non-removably coupled to hub 22a. Such non-removable coupling of vascular graft 14 to hub 22a can be accomplished in any suitable fashion, such as, for example, via a crimped connection (e.g., a connection facilitated by permanent deformation of at least a portion of the hub and/or at least a portion of the vascular graft, for example, permanent deformation of proximal end 30 of the hub while the vascular graft is disposed within recess 64 such that the vascular graft is clamped within the recess by the proximal end of the hub), a welded connection (e.g., a connection facilitated by fusing together of at least a portion of the hub and least a portion of the vascular graft), adhesives, and/or the like. At least through such non-removable coupling of a respective vascular graft (e.g., 14) and a respective hub (e.g., 22a), the present apparatuses (e.g., 10a) may be configured to facilitate a fluid-tight coupling between the respective vascular graft and the respective hub, for use as a permanent implant, and/or the like.

In this embodiment, apparatus 10a comprises a penetrator 66 configured to penetrate (e.g., be disposed into, but not necessarily through) a wall of a blood vessel. For example, in the depicted embodiment, penetrator 66 has a distal end 70 which tapers to a tip 74. In at least this way, as penetrator 66 penetrates a wall of a blood vessel, tapered distal end 70 of the penetrator may dilate an opening in the wall of the blood vessel (e.g., whether the opening is made by tip 74 of the penetrator, a guide wire 90, and/or the like) (e.g., facilitating a seal between the penetrator and the wall of the blood vessel, which may minimize blood loss during insertion of the penetrator, obviate the need for vascular clamping and/or occlusion of the blood vessel, and/or the like). In the depicted embodiment, penetrator 66 defines an interior passageway 86 sized for a guide wire 90 (FIGS. 3A-3B) (e.g., any suitable guide wire, such as, for example, a guide wire having a core diameter of 0.014, 0.018, or 0.035 inches), such that, for example, the guide wire may be used to guide the penetrator to an insertion site on a blood vessel.

In the embodiment shown, penetrator 66 is disposable through lumen 18 of vascular graft 14 and through interior passageway 38 of hub 22*a* (FIG. 1B). In this embodiment, interior passageway 38 of hub 22*a* is substantially (e.g., physically) blocked by penetrator 66 when the penetrator is disposed through the interior passageway of the hub; for example, at least a portion of the penetrator has dimensions that correspond to a section of the interior passageway of the hub within which the portion of the penetrator is disposable. In at least this way, penetrator 66 may minimize blood loss through interior passageway 38 of hub 22*a* during securement of the hub to a blood vessel, which may obviate the need for vascular clamping and/or occlusion of the blood vessel, and/or the like.

In the depicted embodiment, penetrator 66 is removably couplable to hub 22*a* such that rotation of the penetrator rotates the hub. For example, in the embodiment shown, penetrator 66 is configured (e.g., sized) for frictional coupling with hub 22*a* (e.g., between an exterior surface of the penetrator and an interior surface of the hub). To illustrate, in this embodiment, penetrator 66 may be disposed within interior passageway 38 of hub 22*a* such that a frictional force between an exterior surface of the penetrator and an interior surface of the hub is sufficient to allow for rotation of the hub (e.g., within and/or into a wall of a blood vessel) in response to rotation of the penetrator, yet insufficient to undesirably impede removal of the penetrator from the interior passageway through proximal end 30 of the hub. In some embodiments, an interior passageway (e.g., 38) of a respective hub (e.g., 22*a*) may taper in a transverse dimension (e.g., 78) along a direction (e.g., generally indicated by arrow 62) from a proximal end (e.g., 30) to a distal end (e.g., 26) of the respective hub (e.g., such that a frictional force between an exterior surface of a respective penetrator 66 and an interior surface of the respective hub increases as the respective penetrator is moved within and relative to the respective hub in a direction from the proximal end to the distal end of the respective hub). In yet other embodiments, any suitable structure can be used to accomplish such a removable and rotatable coupling between a respective penetrator (e.g., 66) and a respective hub (e.g., 22*a*), such as, for example, interlocking features (e.g., a key and keyway structure) of the respective penetrator and the respective hub, and/or the like.

Referring additionally to FIGS. 3A-3D, shown are some steps of one embodiment of the present methods. While not required in all embodiments, in the embodiment shown, a guide wire (e.g., 90) may be inserted into a wall of a blood vessel (FIG. 3A). In this embodiment, the guide wire may be disposed through an interior passageway (e.g., 86) of a penetrator (e.g., 66) of one of the present apparatuses (e.g., 10*a*) (e.g., when the penetrator is disposed within a hub 22*a* of the apparatus) such that the guide wire may function to guide the penetrator and apparatus to an insertion site on the blood vessel (FIG. 3B).

In the depicted embodiment, a tapered distal end (e.g., 70) of the penetrator may be inserted into the wall of the blood vessel through an opening, for example, an opening made by a tip (e.g., 74) of the penetrator or, if present, by the guide wire, and the penetrator may be advanced into the wall of the blood vessel to dilate the opening (e.g., facilitating a seal between the penetrator and the wall of the blood vessel). In the embodiment shown, the penetrator may be advanced into the wall of the blood vessel until the hub engages (e.g., contacts or penetrates) the wall of the blood vessel (e.g., FIG. 3B).

In this embodiment, the hub may be rotated (e.g., generally along a direction indicated by arrow 94) relative to the blood vessel (e.g., by rotating the penetrator, which may be rotatably (e.g., frictionally) engaged with the hub) such that one or more helical protrusions (e.g., 54) extending away from a (e.g., tapered) wall (e.g., 34) of the hub engage the wall of the blood vessel to secure the hub relative to the blood vessel (FIG. 3C) (e.g., via radial forces between the wall of the blood vessel and the wall of the hub and/or compressive forces between the wall of the blood vessel and adjacent portions of one or more helical protrusions). In some embodiments, the hub may be secured relative to the blood vessel via one or more sutures, which may be disposed through one or more openings defined by the hub (e.g., defined by a flange 42 defined by the proximal end of the hub).

In the depicted embodiment, the penetrator (e.g., and guide wire, if present) may be removed from the interior passageway of the hub through the lumen of the vascular graft, thereby enabling fluid flow through the interior passageway of the hub and through the lumen of the vascular graft (FIG. 3D). In some embodiments, the vascular graft may be temporarily clamped (e.g., to inhibit blood flow through the lumen of the vascular graft) (e.g., pending completion of a bypass or anastomosis procedure using the vascular graft).

Figure 4C:
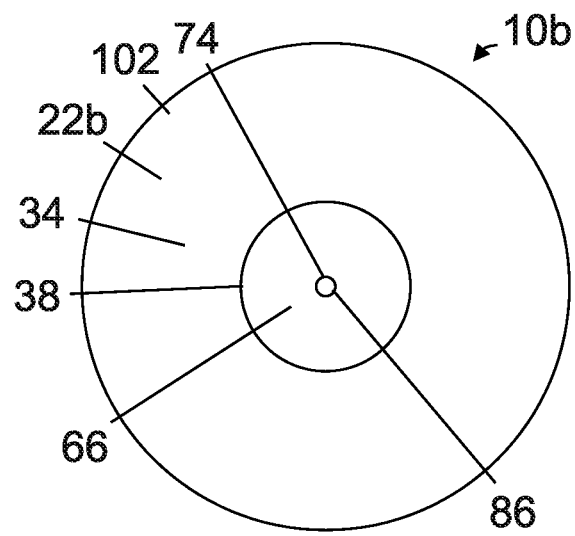

Referring now to FIGS. 4A-4C, shown therein and designated by the reference numeral 10*b* is a second embodiment of the present apparatuses. Apparatus 10*b* may be substantially similar to apparatus 10*a*, with the primary exception being that hub 22*b* of apparatus 10*b* is configured to be secured relative to a blood vessel via an annular recess 106 (e.g., as opposed to one or more helical protrusions (e.g., 54)). Otherwise, apparatus 10*b* may include any and/or all of the features described above with respect to apparatus 10*a*. For example, in the embodiment shown, apparatus 10*b* comprises a hub 22*b* having a distal end 26 configured to penetrate a blood vessel, a proximal end 30, and a wall 34 extending between the distal end and the proximal end that defines (e.g., via an interior surface 98 of the wall) an interior passageway 38.

In this embodiment, wall 34 is configured to facilitate securement and/or placement of hub 22*b* relative to a blood vessel. For example, in the depicted embodiment, an outer surface 102 of wall 34 defines an annular recess 106 (e.g., in fixed relation to the wall) that extends around the wall, the recess configured (e.g., dimensioned and located) to receive at least a portion of a wall of a blood vessel (e.g., when the hub is operatively coupled to the blood vessel). To illustrate, in the embodiment shown, distal end 26 of hub 22*b* may be inserted into a wall of a blood vessel, and the hub may be advanced until the wall of the blood vessel, or a portion thereof, reaches recess 106, where the wall of the blood vessel, or portion thereof, may be retained within the recess, whether via resilient characteristics of the wall of the blood vessel, via one or more sutures 116 (described in more detail below), and/or the like. In this embodiment, portions of wall 34 proximal to, or defining a proximal wall of, recess 106 may function as, or may be characterized as, a flange (e.g., 42), in that such portions (which, in some embodiments, may span a larger transverse width than portions of the wall distal to, or defining a distal wall of, the recess) may physically limit a penetration depth of hub 22*b* into a blood vessel by, for example, overlying portions of a wall of the blood vessel, such as portions of the wall of the blood vessel that are disposed within the recess. A hub (e.g., 22*b*) defining an annular recess (e.g., 106) for securement and/or placement of the hub relative to a blood vessel may have a relatively smaller longitudinal length than a hub that employs other securement and/or placement structure(s) (e.g., such as one or more helical protrusions 54 of hub 22*a*). In at least this way, a hub defining an annular recess (e.g., 106) for securement and/or placement of the hub relative to a blood vessel may minimize a portion of the hub that is disposed into the blood vessel when the hub is operatively coupled to the blood vessel (e.g., thus minimizing flow restrictions within the blood vessel due to presence of the hub).

In the depicted embodiment, wall 34, and more particularly, recess 106, is configured to resist removal hub 22*b* from a blood vessel. For example, in the embodiment shown, at least because recess 106 has a smaller transverse width than portions of wall 34 distal to, or defining a distal wall of, the recess and portions of the wall proximal to, or defining a proximal wall of, the recess, once a wall of a blood vessel, or a portion thereof, is disposed within the recess, wall 34 may physically resist separation of the hub and the wall of the blood vessel. In this embodiment, hub 22*b*, and more particularly, wall 34, defines one or more structures that may function as, or may be characterized as, barb(s) (e.g., whether having rounded and/or sharp edges), such that, for example, hub 22*b*, or a portion thereof, resembles a barbed hose fitting. For example, in the depicted embodiment, a distal-most portion 108 of wall 34 within recess 106 is tangent to a line that is angularly disposed at an angle 112 of 90 degrees or larger relative to a longitudinal axis 114 of hub 22*b* (FIG. 4A). In at least this way, wall 34, and more particularly, a portion of the wall that defines a distal wall of recess 106, may function to resist separation of hub 22*b* and a blood vessel when the hub is operatively coupled to the blood vessel (e.g., by not encouraging movement of a wall of the blood vessel, or a portion thereof, out of the recess and/or by encouraging movement of the wall of the blood vessel, or a portion thereof, into the recess, as the hub is moved longitudinally away from the blood vessel).

In the embodiment shown, recess 106 is defined by wall 34 of hub 22*b* closer to proximal end 30 of the hub than to distal end 26 of the hub (e.g., to minimize an amount of the hub that is disposed outside of a blood vessel when the hub is operatively coupled to the blood vessel). In this embodiment, wall 34 defines recess 106 such that the recess is rotationally symmetrical about longitudinal axis 114 of hub 22*b*. However, in other embodiments, a recess (e.g., 106) defined by a wall (e.g., 34) of a respective hub (e.g., 22*b*) may be defined in any suitable orientation relative to the respective hub (e.g., the recess may be defined by the wall such that a longitudinal distance between the recess and a proximal end 30 of the hub and/or a longitudinal distance between the recess and a distal end 26 of the hub varies around the hub).

Figures 5A, 5B, 5C:
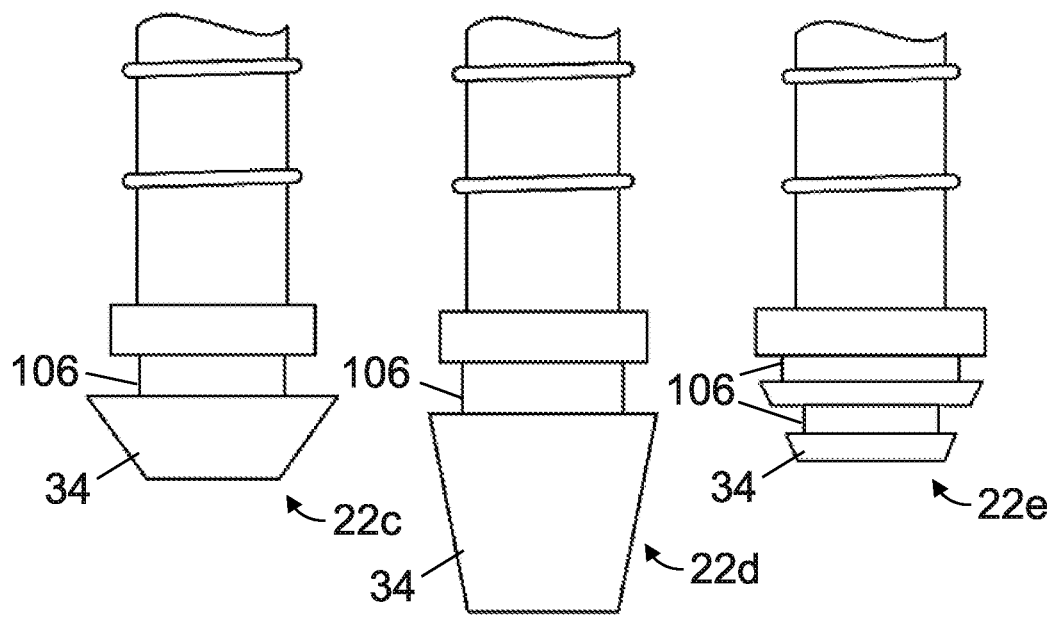
FIGS. 5A-5C are each a side view of a respective hub that may be suitable for use in some embodiments of the present apparatuses.

Referring additionally to FIGS. 5A-5C, shown are side views of hubs 22*c*, 22*d*, and 22*e*, respectively, each of which may be suitable for use in some embodiments of the present apparatuses (e.g., 10*b*). As shown, respective hubs of the present apparatuses may differ from one another in one or more of various ways, including, but not limited to: (1) longitudinal lengths (e.g., hub 22*d* has a larger longitudinal length than hubs 22*c* and 22*e*); (2) maximum transverse widths (e.g., hub 22*c* has a larger maximum transverse width than hubs 22*d* and 22*e*); (3) taper of respective walls 34 (e.g., hub 22*d* has a wall with a more gradual taper than respective walls of hubs 22*c* and 22*e*); (4) number of respective recess(es) 106 (e.g., hub 22*e* defines two recesses and hubs 22*c* and hub 22*d* each define one recess 106); (5) dimensions of respective recess(es) 106 (e.g., a longitudinal length spanned by a respective recess 106 is larger for hub 22*d* than for hubs 22*c* and 22*e*, and a maximum transverse width within a respective recess 106 is larger for hub 22*e* than for hubs 22*c* and 22*d*); and/or the like.

Figure 6:
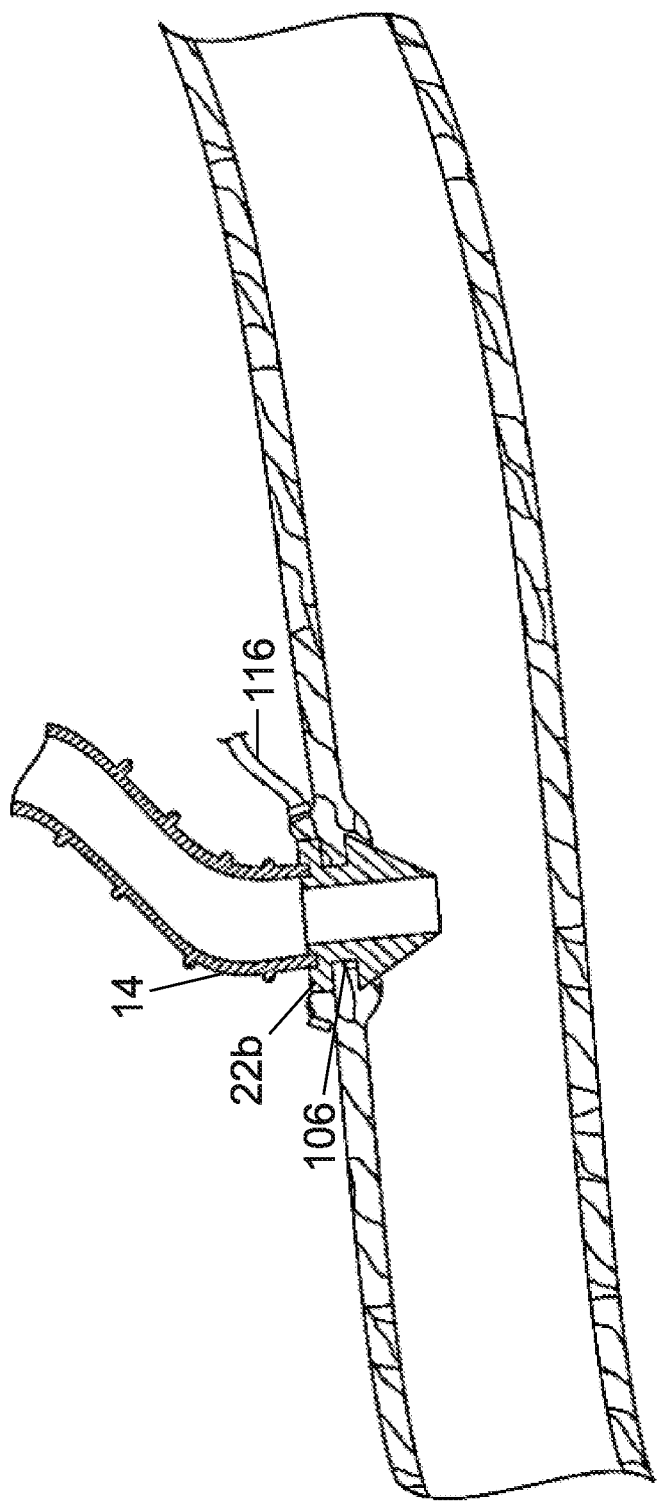
FIG. 6 depicts a step of one embodiment of the present methods.

Referring additionally to FIG. 6, shown is a step of one embodiment of the present methods. The method depicted in FIG. 6 may be similar to the method depicted in FIGS. 3A-3D, with the primary exception that the method depicted in FIG. 6 employs an apparatus having a hub (e.g., 22*b*) that defines an annular recess (e.g., 106) (e.g., apparatus 10*b*), and the method depicted in FIGS. 3A-3D employs an apparatus having a hub (e.g., 22*a*) with one or more helical protrusions (e.g., 54) (e.g., apparatus 10*a*). For example, the method depicted in FIG. 6 may include the use of a penetrator (e.g., 66) and may include the use of a guide wire (e.g., 90), in a same or similar fashion as described above and shown in FIGS. 3A, 3B, and 3D.

In the embodiment shown, a distal end (e.g., 26) of hub (e.g., 22*b*) may be inserted into a wall of a blood vessel, and the hub may be longitudinally advanced (but not necessarily rotated relative to the blood vessel) until the wall of the blood vessel, or a portion thereof, reaches the recess, where the wall of the blood vessel, or a portion thereof, may be retained within the recess. For example, in this embodiment, the wall of the blood vessel, or a portion thereof, may be urged into the recess of the hub (e.g., such that radial forces between the wall of the blood vessel and the wall of the hub and/or compressive forces between the wall of the blood vessel and portions of the wall of the hub within the recess may operate to facilitate securement and/or a seal between the wall of the blood vessel and the hub). More particularly, in the depicted embodiment, the wall of the blood vessel, or a portion thereof, may be urged into the recess by tensioning one or more sutures 116, which may be disposed into the wall of the blood vessel and around at least a portion of (e.g., up to and including all of) the hub. In some embodiments, such sutures 116 may be disposed into the wall of the blood vessel before the hub, penetrator, or guide wire penetrate the blood vessel.

Some embodiments of the present apparatuses may be included in some embodiments of the present kits. Some of the present kits may include a container (e.g., a tray (e.g., a sealed tray), a box, or a pouch (e.g., a sealed and/or flexible pouch)) in which components (e.g., vascular graft(s) 14, hub(s) 22*a*, 22*b*, 22*c*, 22*d*, 22*e*, penetrator(s) 66, and/or the like) of one or more of the present apparatuses (e.g., 10*a*, 10*b*) are disposed. For example, some embodiments of the present kits include a vascular graft (e.g., 14) defining a lumen (e.g., 18) and a hub (e.g., 22*a*) having a distal end (e.g., 26), a proximal end (e.g., 30), a wall (e.g., 34) extending between the distal end and the proximal end that defines an interior passageway (e.g., 38), and one or more helical protrusions (e.g., 54) fixed in relation to the wall, each extending away from the interior passageway, where the vascular graft is non-removably coupled to the hub, and the lumen of the vascular graft is in communication with the interior passageway of the hub. For further example, some embodiments of the present kits include a vascular graft (e.g., 14) defining a lumen (e.g., 18) and a hub (e.g., 22b) having a distal end (e.g., 26), a proximal end (e.g., 30), and a wall (e.g., 34) extending between the distal end and the proximal end, the wall having an inner surface (e.g., 98) defining an interior passageway (e.g., 38) and an outer surface (e.g., 102) defining an annular recess (e.g., 106) that extends around the wall, where the vascular graft is non-removably coupled to the hub, and the lumen of the vascular graft is in communication with the interior passageway of the hub. Some kits include a penetrator (e.g., 66) defining an interior passageway (e.g., 86) sized for a guide wire (e.g., 90). Some kits include a guide wire (e.g., 90).

Some of the present kits may include instructions for use, for example, on the outside of the container (e.g., on a sticker) or on material disposed inside the container (e.g., a written insert). In some of the present kits, one or more components of one or more apparatuses (e.g., 10a) may be sterile.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for securing a distal end of a vascular graft to a blood vessel, the method comprising:
    inserting a distal end of a penetrator into a blood vessel such that the penetrator contacts the blood vessel, the penetrator disposed within a lumen of the vascular graft and within an interior passageway of a hub coupled to the vascular graft, the hub having:
        a distal end configured to penetrate the blood vessel;
        a proximal end;
        a wall extending between the distal end and the proximal end that defines the interior passageway; and
        one or more helical protrusions fixed in relation to the wall, each extending away from the interior passageway;
    rotating the penetrator relative to the blood vessel to secure the hub within the blood vessel;
    removing the penetrator from the interior passageway of the hub and through the lumen of the vascular graft; and
    attaching a proximal end of the vascular graft to an anatomical structure such that the blood vessel and the anatomical structure are in fluid communication with one another via the vascular graft.

2. The method of claim 1, comprising suturing the hub to the blood vessel.

3. The method of claim 1, comprising temporarily clamping the vascular graft.

4. The method of claim 1, wherein a portion of the wall that is disposed between a proximal-most portion of the helical protrusion(s) and a distal-most portion of the helical protrusion(s) tapers in an exterior transverse dimension along a direction from the proximal end of the hub toward the distal end of the hub.

5. The method of claim 1, wherein the penetrator defines an interior passageway that extends through the distal end of the penetrator and is sized for a guide wire.

6. The method of claim 1, wherein the vascular graft is non-removably coupled to the hub.

7. The method of claim 1, wherein the vascular graft has a length that is at least 14 centimeters (cm).

8. The method of claim 1, wherein, for each of the helical protrusion(s), a longitudinal distance between adjacent portions of the helical protrusion decreases along a direction from the distal end of the hub to the proximal end of the hub.

9. The method of claim 1, wherein the proximal end of the hub defines a flange.

10. The method of claim 9, wherein the flange defines one or more openings, each configured to receive a suture.

11. The method of claim 1, wherein:
    the distal end of the hub has a first transverse dimension; and
    the proximal end of the hub has a second transverse dimension that is larger than the first transverse dimension.

12. The method of claim 1, wherein the interior passageway of the hub tapers in a transverse dimension along a direction from the proximal end of the hub to the distal end of the hub.

13. The method of claim 1, wherein the hub is monolithic.

14. The method of claim 1, wherein the vascular graft is coupled to the hub such that at least a portion of the hub is received within the lumen of the vascular graft.

15. The method of claim 1, wherein the vascular graft is crimped to the hub.

16. The method of claim 1, wherein the vascular graft is welded to the hub.

17. The method of claim 1, wherein the vascular graft comprises woven polyester and/or expanded polytetrafluoroethylene.

* * * * *